United States Patent
Ahmed et al.

(10) Patent No.: US 12,173,184 B1
(45) Date of Patent: Dec. 24, 2024

(54) SELENATED THIOUREA-BASED HYBRID COMPOUNDS AS CORROSION INHIBITORS FOR STEEL PIPELINES

(71) Applicant: KING FAISAL UNIVERSITY, Al-Ahsa (SA)

(72) Inventors: Hany Mohamed Abd El-Lateef Ahmed, Al-Ahsa (SA); Saadeldin Elsayed Ibrahim Shabaan, Al-Ahsa (SA); Mai Mostafa Khalaf Ali, Al-Ahsa (SA); Mohamed Gouda, Al-Ahsa (SA); Ibrahim Mohamed Abdelhalim Mohamed, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 12 days.

(21) Appl. No.: 18/621,561

(22) Filed: Mar. 29, 2024

Related U.S. Application Data

(62) Division of application No. 18/242,809, filed on Sep. 6, 2023, now Pat. No. 11,970,630.

(51) Int. Cl.
 C09D 5/08 (2006.01)
 C07C 391/02 (2006.01)
 C23F 11/04 (2006.01)

(52) U.S. Cl.
 CPC ............ *C09D 5/086* (2013.01); *C07C 391/02* (2013.01); *C23F 11/04* (2013.01)

(58) Field of Classification Search
 None
 See application file for complete search history.

(56) References Cited

U.S. PATENT DOCUMENTS

2014/0155641 A1  6/2014  Hanes
2017/0027168 A1  2/2017  Heath

OTHER PUBLICATIONS

El-Lateef et al. "Corrosion mitigation characteristics of some novel organoselenium thiourea derivatives for acid pickling of C1018 steel via experimental and theoretical study", Sci Rep. Jun. 3, 2023; 13: 9058.
Wang et al., "Synthesis, Characterization and Corrosion Inhibition Performance of the Thiourea-chitosan in Acidic Medium", Int. J. Electrochem. Sci., 14 (2019) 8852-8868.

*Primary Examiner* — Jeffrey D Washville
(74) *Attorney, Agent, or Firm* — Nath, Goldberg & Meyer; Joshua B. Goldberg

(57) ABSTRACT

New selenated thiourea hybrid compounds are described herein, as well as the use of such selenated thiourea hybrid compounds in inhibiting corrosion of a steel material. Also described are methods for forming the new selenated thiourea hybrid compounds as well as anti-corrosion coatings containing the selenated thiourea hybrid compounds.

5 Claims, 1 Drawing Sheet

SELENATED THIOUREA-BASED HYBRID COMPOUNDS AS CORROSION INHIBITORS FOR STEEL PIPELINES

CROSS-REFERENCE TO RELATED APPLICATION

This application is a divisional of U.S. patent application Ser. No. 18/242,809, filed on Sep. 6, 2023, the entire contents of which are incorporated herein by reference.

BACKGROUND

1. Field

The disclosure of the present patent application relates to novel selenated thiourea hybrid compounds and the use of the same for inhibiting corrosion in stainless steel.

2. Description of the Related Art

Due to their low costs and superior mechanical properties, carbon steels, particularly C1018 steel, are frequently used in the petroleum sector in a variety of manufacturing processes, including chemical processing, construction, casing, and developing oil/gas pipelines. However, C1018 steel is highly susceptible to erosion in sweet oilfield-generated water.

The most corrosive and frequent media in the production of petroleum is $CO_2$, which is an obviously occurring or purposefully inserted ingredient in the presence of a high Cl-ion dose. Carbonic acid ($H_2CO_3$) is created when $CO_2$ dissolves in water. This acid interacts with C1018 steel and causes corrosion. The inner corrosion protection of C1018 steel is difficult to screen, which may result in failures, an ecological catastrophe, and impressive accidents.

The most widely used method of avoiding abrasion on steel and steel alloys is the application of inhibitors. Chromate-based conversion coatings and paints have been utilized to protect steel surfaces against corrosion because of the active corrosion prevention capabilities of these compounds. However, chromate-based coatings are no longer used because of their high carcinogenicity and toxicity. As a result, chromate-free, environmentally acceptable, and passable anti-erosion pre-treatments are becoming more and more necessary. The use of organic inhibitors could provide a solution to the corrosion issue that works by altering the corrosive media.

Therefore, developing new products solving the aforementioned problems are highly desired for inhibiting steel corrosion, particularly in the petrochemical industries.

SUMMARY

The present subject matter relates to the protection of steel pipelines against corrosion. Organic inhibitors based on diorganyl diselenide, or organyl selenides, are a favored solution for preventing corrosion because of their versatility and low cost. In this regard, the present subject matter relates to corrosion protection of steel with eco-friendly less expensive corrosion inhibitors based on diorganyl diselenides or organyl selenides, for example, the development and synthesis of novel thiourea-based selenated hybrid compounds. The creation of these compounds and their structures were confirmed via different spectroscopic instruments. The inhibiting influence of the prepared molecules on steel pipeline corrosion in $CO_2$-saturated 3.5% NaCl was examined by diverse methods including electrochemical impedance spectroscopy (EIS) and potentiodynamic polarization (PDP). The inhibition efficiency of the compounds was observed at ~98.17% at 0.2 mM. The selenated thiourea hybrid compounds can function as mixed-type inhibitors according to PDP investigations. The Langmuir isotherm describes the adsorption of selenated thiourea hybrid on the metal surface. Accordingly, the current novel corrosion inhibitors can be used for steel pipelines in $CO_2$-saturated NaCl for petroleum companies.

In an embodiment, the present subject matter relates to a selenated thiourea hybrid compound of the formula I or the formula II:

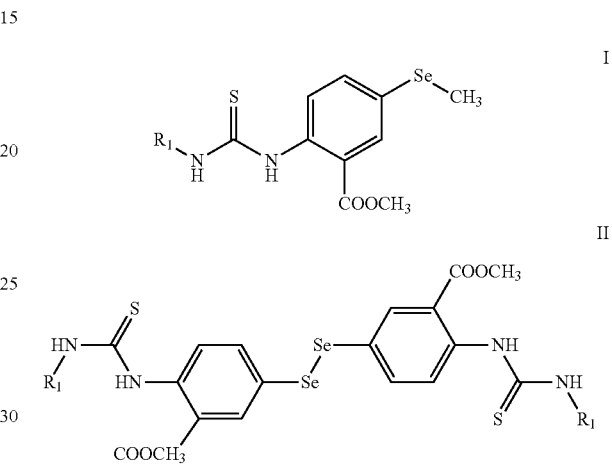

wherein: each $R^1$ is independently methyl or phenyl.

In another embodiment, the present subject matter relates to an anticorrosion coating comprising the selenated thiourea hybrid compound of the formula I or the formula II.

In a further embodiment, the present subject matter relates to a method of inhibiting corrosion in a steel material, the method comprising: providing a $CO_2$-saturated brine the $CO_2$ saturated brine further comprising the selenated thiourea hybrid compound of formula I or the selenated thiourea hybrid compound of formula II; contacting a surface of the steel material with the $CO_2$-saturated brine; adsorbing the selenated thiourea hybrid compound of formula I or the selenated thiourea hybrid compound of formula II on the surface of the steel material; and inhibiting corrosion of the steel material.

In an additional embodiment, the present subject matter relates to a method of making a selenated thiourea hybrid compound, the method comprising: reacting equimolar amounts of dimethyl 5,5'-diselanediylbis(2-aminobenzoate) and $R_1$—N=C=S in ethanol, wherein $R_1$ is methyl or phenyl; and obtaining the selenated thiourea hybrid compound, wherein the selenated thiourea hybrid compound has the formula I:

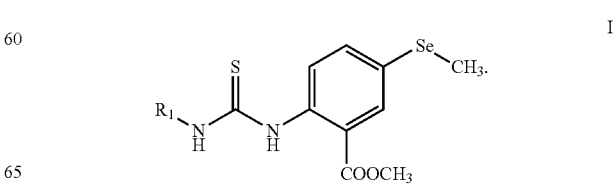

In an additional embodiment, the present subject matter relates to a method of making a selenated thiourea hybrid compound, the method comprising: reacting equimolar amounts of methyl 2-amino-5-(methylselanyl)benzoate and $R_1$—N═C═S in ethanol, wherein $R_1$ is methyl or phenyl; and obtaining the selenated thiourea hybrid compound, wherein the selenated thiourea hybrid compound has the formula II:

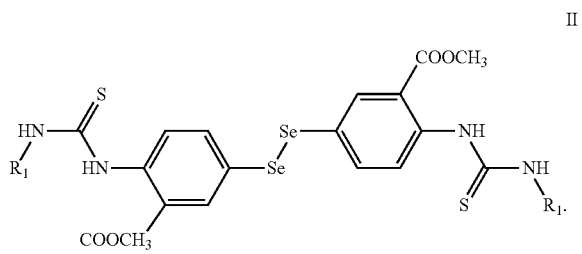

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION OF THE PREFERRED EMBODIMENTS

Figure 1:
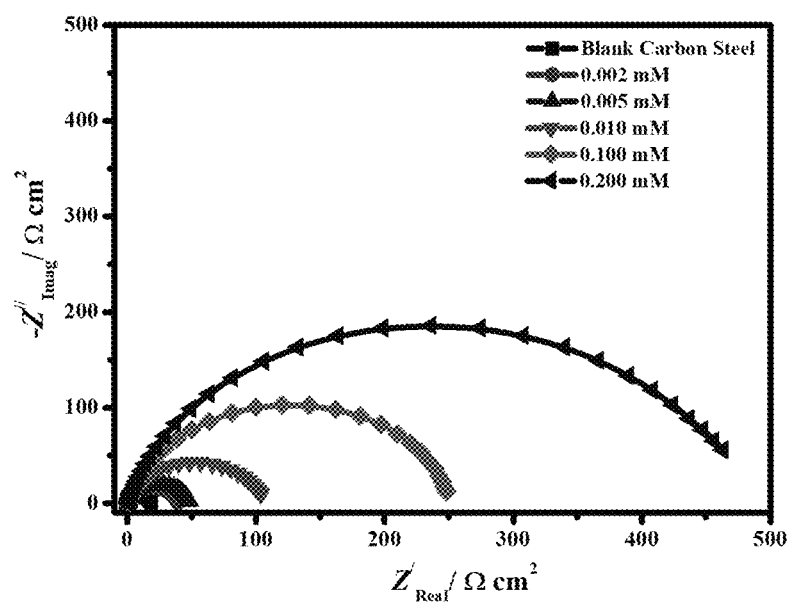
FIG. 1 is a Nyquist plot of C1018 steel electrode in blank $CO_2$-saturated NaCl solution and with the addition of varying concentrations of the present selenated thiourea hybrids at 298 K.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to the protection of steel pipelines against corrosion. Organic inhibitors based on diorganyl diselenide, or organyl selenides, are a favored solution for preventing corrosion because of their versatility and low cost. In this regard, the present subject matter relates to corrosion protection of steel with eco-friendly less expensive corrosion inhibitors based on diorganyl diselenides or organyl selenides, for example, the development and synthesis of novel thiourea-based selenated hybrid compounds.

The creation of these compounds and their structures were confirmed via different spectroscopic instruments. The inhibiting influence of the prepared molecules on steel pipeline corrosion in $CO_2$-saturated 3.5% NaCl was examined by diverse methods including electrochemical impedance spectroscopy (EIS) and potentiodynamic polarization (PDP). The inhibition efficiency of the compounds was observed at ~ 98.17% at 0.2 mM. The selenated thiourea hybrid compounds can function as mixed-type inhibitors, according to PDP investigations. The Langmuir isotherm describes the adsorption of selenated thiourea hybrid on the metal surface. Accordingly, the current novel corrosion inhibitors can be used for steel pipelines in $CO_2$-saturated NaCl for petroleum companies.

In an embodiment, the present subject matter relates to a selenated thiourea hybrid compound of the formula I or the formula II:

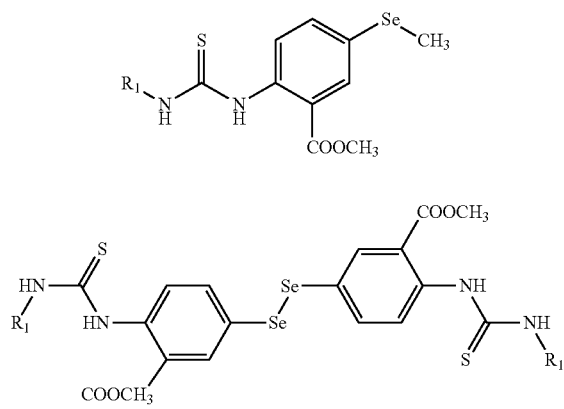

wherein: each $R^1$ is independently methyl or phenyl.

In an embodiment, in the compound of formula II, for each instance of $R_1$ can be the same.

In another embodiment, the selenated thiourea hybrid compound can be selected from the group consisting of: dimethyl 5,5'-diselanediylbis(2-(3-phenylthioureido)benzoate) (2); dimethyl 5,5'-diselanediylbis(2-(3-methylthioureido)benzoate) (3); methyl 5-(methylselanyl)-2-(3-phenylthioureido)benzoate (5); and methyl 5-(methylselanyl)-2-(3-methylthioureido)benzoate (6).

In another embodiment, the present subject matter relates to an anticorrosion coating comprising the selenated thiourea hybrid compound of the formula I or the formula II.

In an embodiment of the present anticorrosion coating, the selenated thiourea hybrid compound can be adsorbed on a surface of a steel material.

In another embodiment of the present anticorrosion coating, the steel material can comprise stainless steel or C1018 steel.

In certain embodiments, the anticorrosion coating can be a preservation layer that serves as an isolating barrier between the metal contact and the hostile environment as provided by the instant organic films. The selenated thiourea hybrid-based films as described herein can be used as corrosion inhibitors to produce stable films on steel surfaces.

In a further embodiment, the present subject matter relates to a method of inhibiting corrosion in a steel material, the method comprising: providing a $CO_2$-saturated brine the $CO_2$ saturated brine further comprising the selenated thiourea hybrid compound of formula I or the compound of formula II; contacting a surface of the steel material with the $CO_2$-saturated brine; adsorbing the selenated thiourea hybrid compound of formula I or the selenated thiourea hybrid compound of formula II on the surface of the steel material; and inhibiting corrosion of the steel material.

In an embodiment of the present methods, the $CO_2$-saturated brine can further comprise 3.5% NaCl. In another embodiment of the present methods, the $CO_2$-saturated brine can comprise sweet-oilfield generated water.

In one aspect of the present methods, the method can provide up to an about 68%, about 85%, about 93%, about 86%, or about 98% inhibition efficiency, or can provide an about 96% or an about 98% corrosion inhibition efficiency at 0.2 mM.

In another embodiment, the inhibiting corrosion can comprise preventing the surface of the steel material from dissolving in the $CO_2$-saturated brine.

In a further embodiment, the adsorbing the selenated thiourea hybrid compound on the surface of the steel material can form a protective layer on the surface of the steel material.

In an additional embodiment, the steel material used in the present inhibition methods can comprise stainless steel or C1018 steel.

In an additional embodiment, the present subject matter relates to a method of making a selenated thiourea hybrid compound, the method comprising: reacting equimolar amounts of dimethyl 5,5'-diselanediylbis(2-aminobenzoate) and $R_1$—N═C═S in ethanol, wherein $R_1$ is methyl or phenyl; and obtaining the selenated thiourea hybrid compound, wherein the selenated thiourea hybrid compound has the formula I:

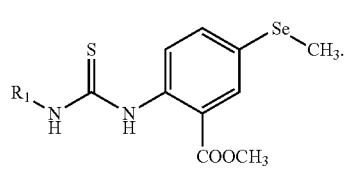

In an additional embodiment, the present subject matter relates to a method of making a selenated thiourea hybrid compound, the method comprising: reacting equimolar amounts of methyl 2-amino-5-(methylselanyl)benzoate and $R_1$—N═C═S in ethanol, wherein $R_1$ is methyl or phenyl; and obtaining the selenated thiourea hybrid compound, wherein the selenated thiourea hybrid compound has the formula II:

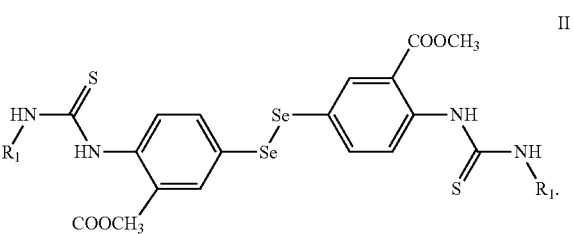

In an embodiment of either production method, the ethanol can be at a temperature of about 75° C. to about 85° C., about 75° C., about 76° C., about 77° C., about 78° C., about 79° C., about 80° C., about 81° C., about 82° C., about 83° C., about 84° C., about 85° C., or at a temperature of about 80° C.

The present production processes can be further summarized according to the following Scheme 1:

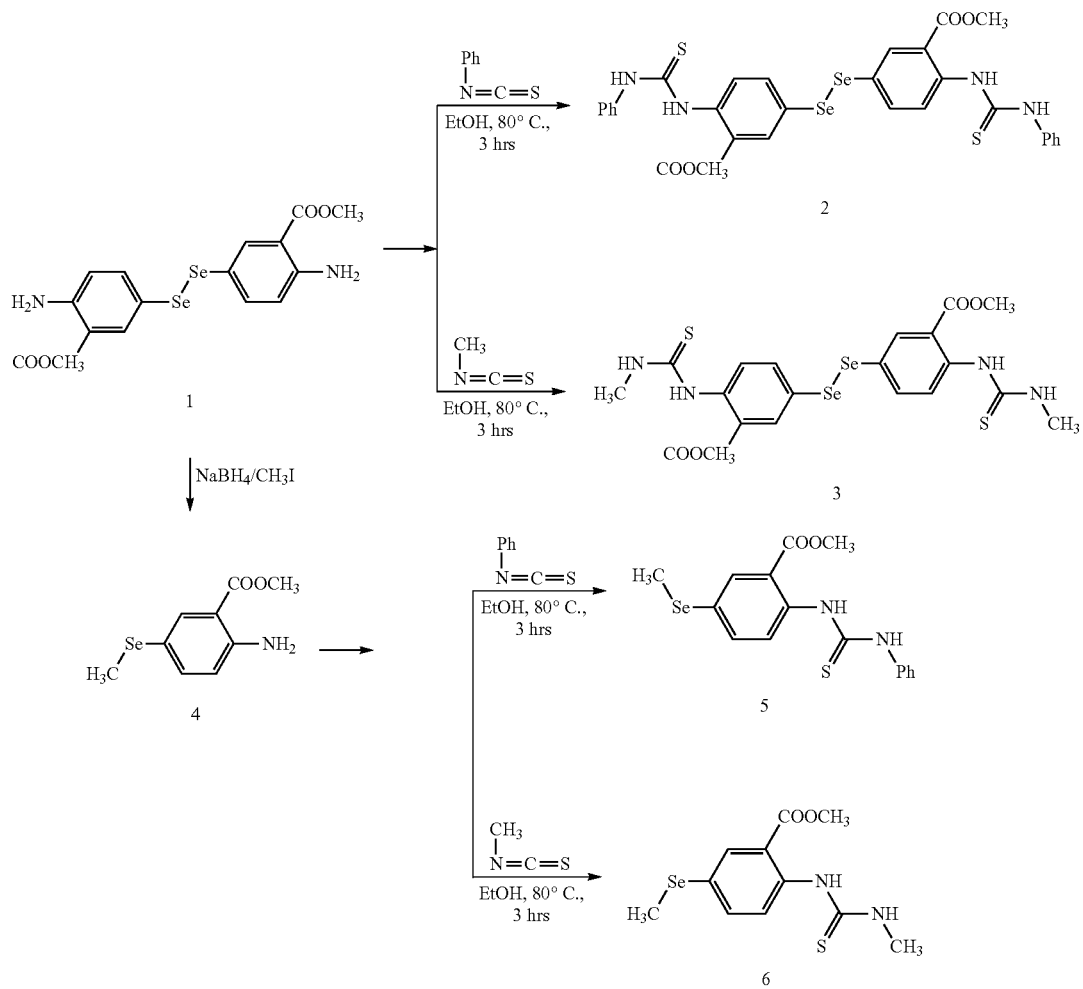

The present teachings are illustrated by the following examples.

EXAMPLES

Example 1

Preparation of Selenated Thiourea Hybrid Compounds (Scheme 1)

Compounds dimethyl 5,5'-diselanediylbis(2-(3-phenylthioureido)benzoate) (2) and dimethyl 5,5'-diselanediylbis(2-(3-methylthioureido)benzoate) (3) were synthesized by the reaction of equimolar amounts of dimethyl 5,5'-diselanediylbis(2-aminobenzoate) (1) with phenyl isothiocyanate and methyl isothiocyanate in ethanol at 80° C., respectively.

Furthermore, compounds methyl 5-(methylselanyl)-2-(3-phenylthioureido)benzoate (5) and methyl 5-(methylselanyl)-2-(3-methylthioureido)benzoate (6) were synthesized by the reaction of equimolar amounts of methyl 2-amino-5-(methylselanyl)benzoate (4) with phenyl isothiocyanate and methyl isothiocyanate in ethanol at 80° C., respectively.

Example 2

EIS Studies/Impedance Analysis

EIS was carried out to further examine the mechanism of selenated thiourea hybrid molecules' corrosion inhibition on C1018 steel. The OCP had reached a stable condition following 60 min of immersion of the C-steel specimen in $CO_2$-saturated NaCl solution without and with various concentrations of selenated thiourea hybrid at 298 K. Based on this, the Nyquist plot for the C-steel electrode at a constant OCP were obtained and are shown in FIG. 1. FIG. 1 clearly shows that all impedance spectra have a single capacitive loop, which demonstrates that the charge transfer process is primarily responsible for controlling the corrosion of C-steel in $CO_2$-saturated NaCl solution with and without inhibitors and is regularly associated with the double-layer performance.

Additionally, these diagrams have an identical curve for all concentrations tested, showing that the corrosion mechanism is unchanged. The frequency dispersion of interfacial impedance may also be to blame for the fact that these Nyquist graphs are not perfect semicircles. Chemical inhomogeneity, surface coarseness, and the adsorption-desorption process of inhibitive molecules on C-steel surfaces all contribute to this phenomenon. Additionally, the semicircle's diameter in the occurrence of the inhibitor is larger than that observed in a blank solution and grows with a growing inhibitor dose, which might be related to the expansion of the surface coverage of inhibitive compounds on the C-steel interface.

The element of CPE is utilized to clarify the capacitance semi-circle depression, which matches surface inhomogeneity resulting from impurities, surface coarseness, grain boundaries, displacements, additive adsorption, development of porous film, etc. The impedance CPE function is characterized by the following Eqn.:

$$Z_{CPE} = \frac{1}{Q(j\omega)^{\alpha}} \quad (1)$$

wherein j represents the imaginary number ($j^2=-1$), Q signifies the CPE magnitude, ω characterizes the angular frequency, and a epitomizes the deviation restriction ($-1 \leq \alpha \leq +1$), which has the significance of a phase shift. The CPE denotes a pure resistor when $\alpha=0$, a pure capacitor when $\alpha=+1$, and an inductor when $\alpha=-1$. Additionally, the following equation was used to get the double-layer capacitances, Cal, for a circuit that has a CPE:

$$C_{dl} = Q(2\pi\omega_{max})^{\alpha-1} \quad (2)$$

where ω max is the maximum frequency value at the imaginary part of the EIS range. The electrochemical parameter values such as $R_s$, $R_p$, and $\eta_E/\%$ (inhibition capacity) of the inhibitor were attained from EIS and recorded in Table 1, below. As the concentration of the inhibitor rises, the $R_p$ values upsurge. The adsorption of inhibitors results in a rise

TABLE 1

EIS corrosion parameters of C1018 steel electrode in the blank molar HCl solution and with the addition of varying concentrations of inhibitor at 298K

| Inhibitor codes | $C_{inh.}$/ mmol/L | $R_s/\Omega$ cm² | $R_p/\Omega$ cm² | θ | Inhibition efficiency/% |
|---|---|---|---|---|---|
| C1018 steel | 0.0 | 0.54 | 18.53 ± 1.1 | — | — |
| Inhibitor | 0.002 | 0.588 | 39.29 ± 2.9 | 0.60698 | 60.69823 |
|  | 0.005 | 0.684 | 48.42 ± 4.6 | 0.68109 | 68.10891 |
|  | 0.010 | 0.828 | 103.73 ± 8.7 | 0.85114 | 85.1136 |
|  | 0.100 | 0.912 | 247.91 ± 16.8 | 0.93771 | 93.77126 |
|  | 0.200 | 1.176 | 463.15 ± 24.2 | 0.96666 | 96.66595 | in $R_p$ values, suggesting a reduction in the exposed surface.

The surface coverage (θ) values could be simply measured from the EIS studies by the ratio inhibition efficiency/100. Therefore, empirical research is required to establish which isotherm best describes the adsorption of inhibitors on the surface of C-steel. Numerous adsorption models such as Langmuir, Frumkin, Freundlich, and Temkin isotherms were characterized. Among the different models of adsorption isotherms tried, the most appropriate one was selected with the help of the correlation coefficient (R2). Langmuir isotherm was found to be the most fitting to the experimental findings, with all correlation coefficient values very close to unity, confirming that the adsorption process of OSe-based compounds on C-Steel in $CO_2$-saturated brine most closely follows the Langmuir isotherm model.

Example 3

FE-SEM Analysis

Figure 2A:
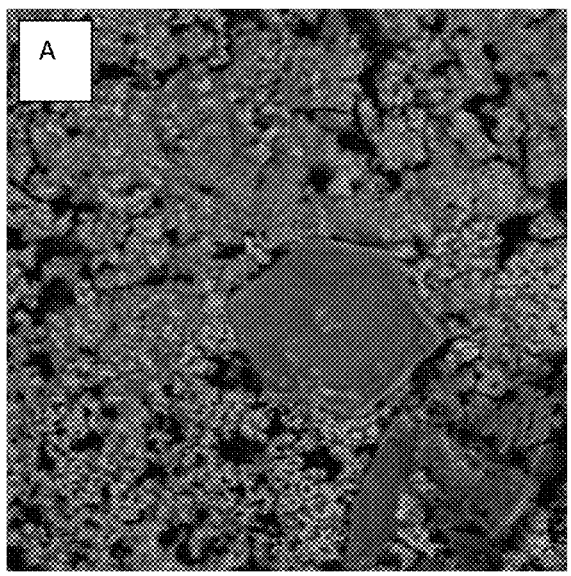
FIGS. 2A and 2B are FE-SEM analysis of C-steel conducted after 20 hours of exposure to blank (2a) solution $CO_2$-saturated brine and 0.2 mM inhibitor (2B) solution $CO_2$-saturated brine.
Figure 2B:
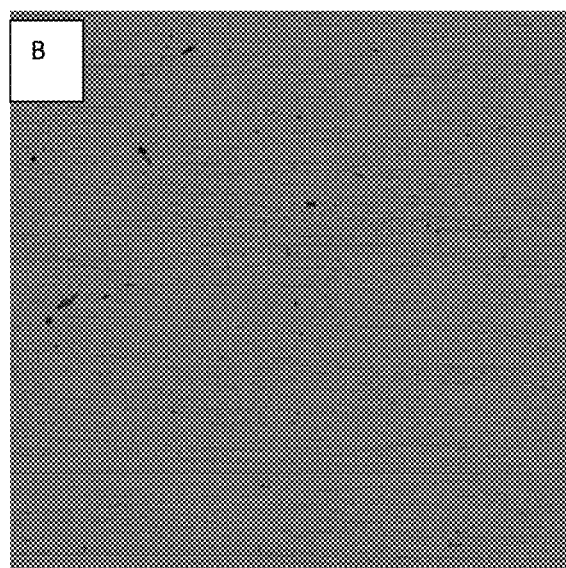

FE-SEM analysis of C-steel conducted after 20 hours of exposure to blank solution $CO_2$-saturated brine and 0.2 mM inhibitor is shown in FIGS. 2A and 2B. The metal surface was severely corroded and degraded, with some pits and deep cavities, as evidenced by close examinations of the FE-SEM image acquired in the absence of the inhibitor (FIG. 2A). The metal sample has a superior morphology and smooth interface compared to the C-steel surface immersed in the blank medium when inhibitor is present (FIG. 2B). According to this, using selenated thiourea hybrid-based films slows down the corrosion rate by preventing C-steel dissolving. This indicates effective corrosion inhibition, the formation of a protective layer that serves as an isolating barrier between the metal contact and the hostile environment.

It is to be understood that the selenated thiourea hybrid compounds, coatings, and methods are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An anticorrosion coating comprising a selenated thiourea hybrid compound of the formula I or the formula II:

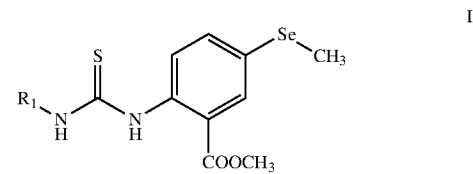

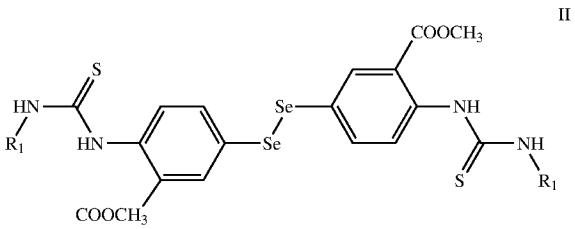

wherein:
each $R^1$ is independently methyl or phenyl.

2. The anticorrosion coating of claim 1, wherein the selenated thiourea hybrid compound is adsorbed on a surface of a steel material.

3. The anticorrosion coating of claim 2, wherein the steel material comprises stainless steel or C1018 steel.

4. The anticorrosion coating of claim 1, wherein, in the compound of formula II, each instance of $R_1$ is the same.

5. The anticorrosion coating of claim 1, wherein the selenated thiourea hybrid compound is selected from the group consisting of:
dimethyl 5,5'-diselanediylbis(2-(3-phenylthioureido)benzoate) (2);

dimethyl 5,5'-diselanediylbis(2-(3-methylthioureido)benzoate) (3);

methyl 5-(methylselanyl)-2-(3-phenylthioureido)benzoate (5); and methyl 5-(methylselanyl)-2-(3-methylthioureido)benzoate (6).

\* \* \* \* \*